United States Patent [19]

Wierzbicki et al.

[11] Patent Number: 5,079,245
[45] Date of Patent: Jan. 7, 1992

[54] 2-TRIFLUOROMETHYL-7-SUBSTITUTE-6,7,8,9-TETRAHYDRO-[5H]-BENZOCY-CLOHEPTENES

[75] Inventors: Michel Wierzbicki, L'Etang la Ville; Pierre Hugon, Rueil Malmaison; Jacques Duhault, Croissy s/Seine; Francoise Lacour, Vincennes, all of France

[73] Assignee: Adir et Compagnie, Neuilly-sur-Seine, France

[21] Appl. No.: 375,591

[22] Filed: Jul. 5, 1989

[30] Foreign Application Priority Data

Jul. 4, 1988 [FR] France .................... 88 08989

[51] Int. Cl.[5] ............... A61K 31/045; A61K 31/075; A61K 31/135; A61K 31/155

[52] U.S. Cl. .................. 514/231.2; 514/239.5; 514/255; 514/318; 514/396; 514/427; 514/510; 514/520; 514/567; 514/569; 514/617; 514/622; 514/625; 514/657; 514/717; 514/729; 544/106; 544/403; 546/205; 548/335; 548/346; 558/426; 560/35; 560/38; 560/43; 560/65; 560/73; 560/105; 560/107; 560/250; 560/255; 562/440; 562/449; 562/452; 562/456; 564/86; 564/179; 564/184; 564/270; 564/428; 564/625; 568/661; 568/808

[58] Field of Search .............. 564/428, 86, 179, 184, 564/270, 625; 544/106, 403; 546/205; 548/335, 346; 558/476; 560/35, 38, 43, 65, 73, 105, 107, 250, 255; 562/440, 449, 452, 456; 568/661, 808; 514/231.2, 239.5, 295, 318, 396, 477, 910, 520, 920, 587, 569, 617, 623, 625, 630, 641, 654, 655, 697, 729

[56] References Cited

U.S. PATENT DOCUMENTS

| | | | |
|---|---|---|---|
| 3,836,534 | 9/1974 | Drukker et al. | 564/428 X |
| 4,091,115 | 5/1978 | Nedblec et al. | 564/428 X |
| 4,128,666 | 12/1978 | Bondinell et al. | 564/428 X |
| 4,132,737 | 1/1979 | Molloy | 564/428 |
| 4,177,292 | 12/1979 | Nedelec et al. | 564/428 X |

Primary Examiner—Richard L. Raymond
Attorney, Agent, or Firm—Gordon W. Hueschen

[57] ABSTRACT

The compounds 2-trifluoromethyl-7-substituted-6,7,8,9-tetrahydro-[5H]-benzocycloheptenes are disclosed and disclosed to be useful in the treatment of metabolic illnesses such as diabetes, obesity, and their complications. A perferred compound is 2-trifluoromethyl-7-amino-6,7,8,9-tetrahydro-[5H-benzocycloheptane.

12 Claims, No Drawings

2-TRIFLUOROMETHYL-7-SUBSTITUTE-6,7,8,9-TETRAHYDRO-[5H]-BENZOCYCLOHEPTENES

The present invention provides benzocycloheptene compounds of the general formula I:

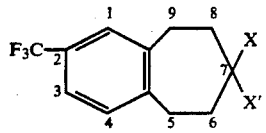
(I)

in which
1) X represents a hydrogen atom, a straight chain or branched alkyl radical having from 1 to 5 carbon atoms, a cyano radical or a hydroxy radical:
2) X' represents:
   a) a hydroxy radical,
   b) a radical OR in which R represents:
      α) and acyl radical COR' in which R' represents a straight chain or branched alkyl radical having from 1 to 5 carbon atoms optionally substituted by a phenyl radical, or a phenyl radical optionally substituted by one or more halogen atoms or alkyl or alkoxy radicals each having from 1 to 5 carbon atoms; or
      β) a atraight chain or branched alkyl radical having from 1 to 5 carbon atoms optionally substituted by a carboxy radical or a phenyl radical;
   c) a radical of the formula:

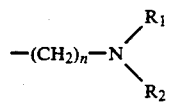

in which:
n represents 0, 1 or 2 and
$R_1$ and $R_2$, which may be the same or different, each represents:
a hydrogen atom;
a straight-chain or branched alkyl radical having from 1 to 5 carbon atoms that is optionally substituted by a hydroxy, amino, carboxy, alkoxycarbonyl having from 1 to 6 carbon atoms or acyloxy radical of the formula R'—COO— in whicch R' has the meaning here above defined;
an alkenyl radical having from 2 to 5 carbon atoms;
an alkynyl radical having from 2 to 5 carbon atoms;
an acyl radical of the formula R"—CO— in which R" represents a straight chain or branched alkyl radical having from 1 to 5 carbon atoms, a phenyl radical or a phenylsulfonylamino radical, the phenyl moiety of which may be optionally substituted by one or more halogen atoms, trifluoromethyl or alkyl or alkoxy radicals each having from 1 to 5 carbon atoms; or
$R_1$ and $R_2$ together with the nitrogen atom to which they are bonded represent
either a group of the formula

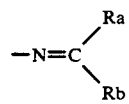

in which:
Ra represents a hydrogen atom or a straight chain or branched alkyl radical having from 1 to 5 carbon atoms, and
Rb represents a hydrogen atom, a straight chain or branched alkyl radical having from 1 to 5 carbon atoms, or a phenyl or phenylalkyl radical;
or a pentagonal or hexagonal heterocyclic radical optionally containing an additional hetero atom: oxygen or nitrogen; or
3) X and X' together represent a radical of the formula:

=N—$R_3$ in which:
$R_3$ represents a straight chain or branched alkyl radical having from 1 to 5 carbon atoms, optionally substituted by:
a cyano radical,
a group —COOR''' in which R''' represents a hydrogen atom or an alkyl radical having from 1 to 5 carbon atoms, or
a phenyl radical, itself optionally substituted by one or more halogen atoms, or alkyl or alkoxy radicals each having from 1 to 5 carbon atoms;
in a racemic form, and the corresponding enantiomers.

The closest prior art to the present invention is illustrated especially
by C. A. (1961) 21066d which mentions 7-aminobenzocycloheptene, which was tested as an antidepressant, cf. J. Pharm. Pharmacol. (1965), 17, 243;
by the French Patent 2 359 608, which concerns, inter alia, 7-aminobenzocycloheptenes of the general formula

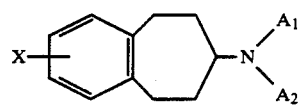

in which
$A_1$ is hydrogen, ($C_1$-$C_5$) alkyl or ($C_2$-$C_5$) alkenyl,
$A_2$ is ($C_1$-$C_5$) alkyl or ($C_2$-$C_5$) alkenyl, or
$A_1$ and $A_2$ form together with the nitrogen atom a saturated heterocycle having from 4 to 6 carbon atoms and optionally an additional hereto atom; and
X is hydrogen or halogen but is never a trifluoromethyl radical; these derivatives are described as antidepressants; and by U.S. Pat. No. 4,185,118, which claims compounds of the general formula:

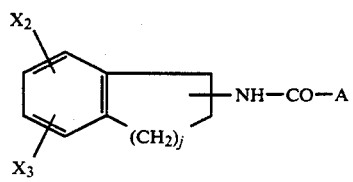

in which j is an integer of from 1 to 4, A is a long chain unsaturated fatty acid radical minus the carboxylic moiety, $X_2$ and $X_3$ are conventional substituents but do not represent a trifluoromethyl radical; these derivatives are described as anti-arteriosclerosis agents.

It may be noted that although included by the general formula, no example of a benzocycloheptene compound is given in this patent; only preparations of indanyl compounds are described therein.

The introduction of a trifluoromethyl substituent at position 2 of the benzene nucleus of known benzocycloheptenes resulted in the production of compounds of the general formula I, the subject of the present invention, and made it possible to illustrate that these compounds (I) have a remarkable activity in the treatment of metabolic illnesses that has not been mentioned for known similar compounds.

The compounds forming the subject of the present application differ from those of the prior art in both their structure and their property, thus giving double assurance of the originality of the present invention.

The present invention also related to a process for the preparation of the compounds of the general formula I, characterised in that: 2-trifluoromethyl-6,7,8,9-tetrahydro-[5H]-benzocyclohepten-7-one of formula II

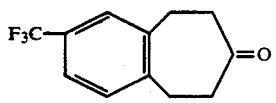
(II)

is reacted:
a) either with a carbonyl compound of the general formula III:

(III)

in which $R_1$ has the meaning given hereinbefore and $R'_1$ represents:
a hydrogen atoms;
a straight chain or branched alkyl radical having from 1 to 4 carbon atoms
in the presence of formic acid, to obtain a compound of the general formula Ia:

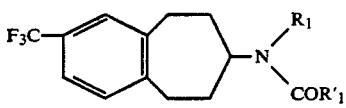
(Ia)

in which $R_1$ and $R'_1$ are as defined hereinbefore, which compound (Ia) may be:
either reduced to yield a compound of the general formula Ib:

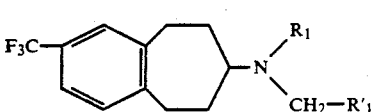
(Ib)

in which $R_1$ and $R'_1$ are as defined hereinbefore, or hydrolysed to yield a compound of the general formula Ic:

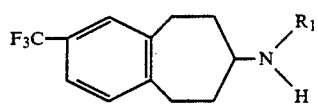
(Ic)

in which $R_1$ is as defined hereinbefore.
b) or with hydroxylamine hydrochloride to yield the oxime of formula

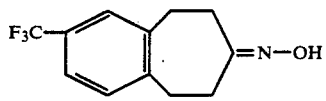

which is hydrogenated under pressure, in the presence of a catalyst such as Raney nickel, in an ammoniacal ethanol medium, to yield the derivative of the formula Id:

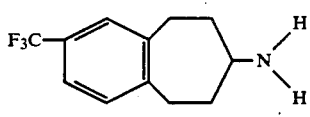
(Id)

This compound (Id) may in turn be transformed by conventional N-substitution methods to yield corresponding secondary and tertiary amines included in the general formula I.

c) or with a compound of the formula IV:

(IV)

in which $R_1$ has the meaning hereinbefore defined, in hydrochloric acid medium, in the presence of an alkaline cyanide, to yield the compound of the formula:

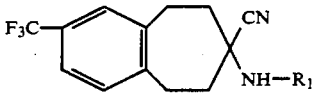

which is transformed in a compound of the formula

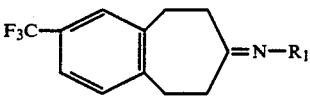

which is itself transformed in a compound of the formula Ie:

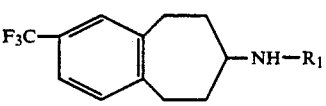
(Ie)

$R_1$ having, in the last three formulae, the meaning hereinbefore defined;
d) or with a compound of the formula V:

(V)

in which R₄ represents a straight chain or branched alkyl radical having from 1 to 5 carbon atoms,
in the presence of magnesium, to yield the compound of the formula:

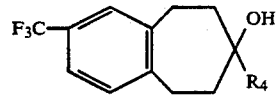

(in which R₄ has the meaning hereinbefore defined) which is treated with a compound of the formula
R₅—CN
(in which R₅ represents a straight chain or branched alkyl radical having from 1 to 4 carbon atoms).
in sulfuric medium, to yield the compound of the formula:

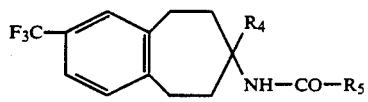

(in which R₄ and R₅ have the meanings hereinbefore defined) which is reduced in a compound of the formula If:

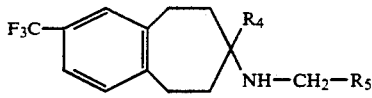

(If)

in which R₄ and R₅ have the meanings hereinbefore defined;

e) or with a compound of the formula VI:

MCN   (VI)

in which M represents an alkaline metal,
in the presence of CH₃COOH and (CH₃CO)₂O, to yield the compound of the formula:

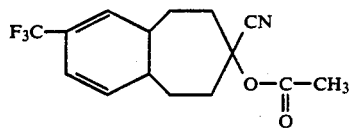

which is, itself:
either treated by Li Al H₄ to yield the compound of the formula Ig:

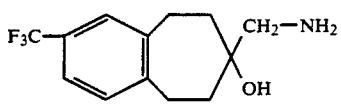

(Ig)

or treated by a base in aqueous medium to yield the compound of the formula:

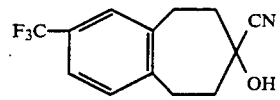

which after dehydration, yield the compound of the formula:

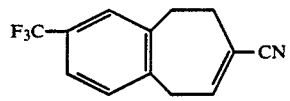

which is itself reduced to yield the compound of the formula Ih:

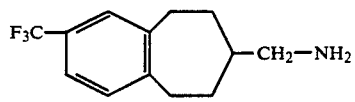

(Ih)

f) or with a compound of the formula VII:

PO (OC₂H₅)₂—CH₂—CN   (VII)

in the presence of a base,
to yield the compound of the formula:

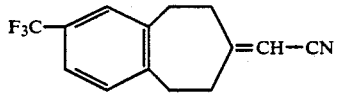

which is itself reduced to yield the compound of the formula Ii:

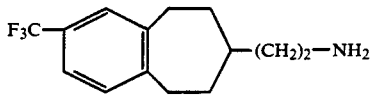

(Ii)

The total of the compounds of the general formulae Ia, Ib, Ic, Id, Ie, If, Ig, Ih, and Ii form the total of the compounds of the general formula I.

If desired, the compounds I obtained in racemic form may be resolved according to conventional methods to obtain the corresponding enantiomers.

The starting material 2-trifluoromethyl-6,7,8,9-tetrahydro-[5H]-benzocyclohepten-7-one of formula II is a new product which as such forms part of the present invention. It may be used as a starting material in the chemical and pharmaceutical industry and especially in the synthesis of 2-trifluoromethyl-6,7,8,9-tetrahydro-[5H]-benzocycloheptene compounds of the general formula I, which are themselves used as medicaments.

This compound of formula II was obtained starting from a commercial product p-trifluoromethyliodobenzene, in accordance with the operating procedure given by way of example hereinafter illustrating the following reaction scheme:

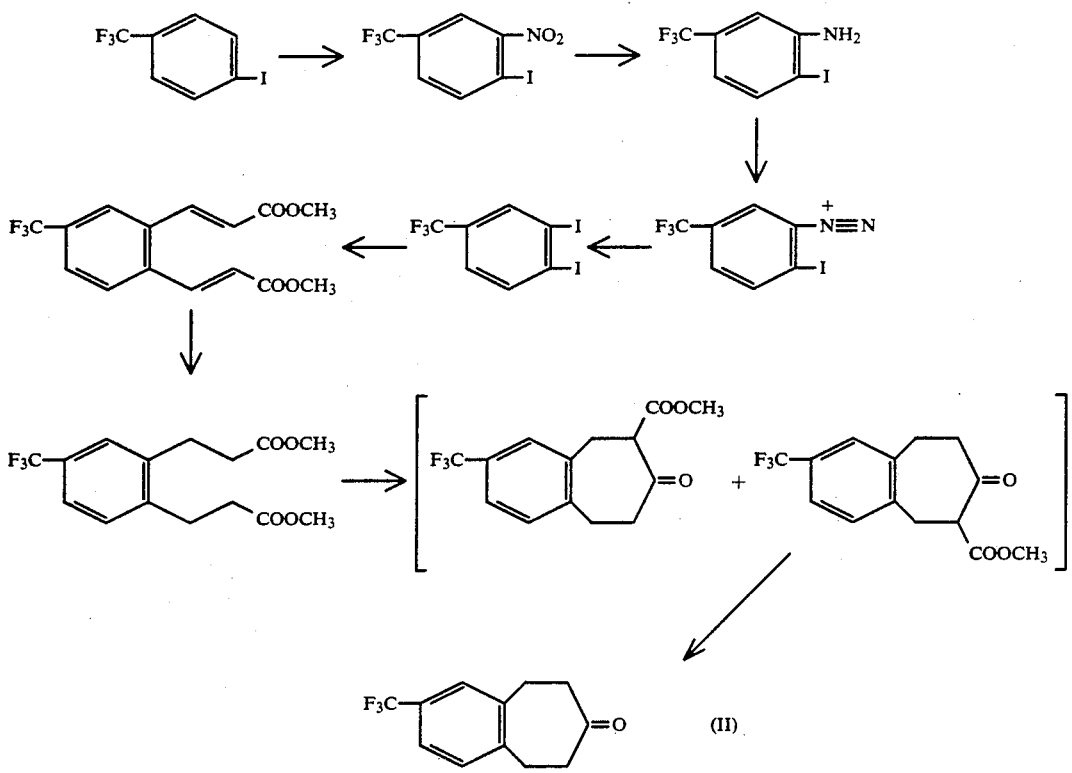

The compounds I containing a basic group may be converted into addition salts with acids, which salts, as such, form part of the present invention. Suitable acids that may be used for the formation of these salts are, in the mineral series: hydrochloric, hydrobromic, sulphuric and phosphoric acid and, in the organic series: acetic, propionic, maleic, fumaric, tartaric, citric, benzoic and methane-sulphonic acid.

The compounds of the general formula I and the physiologically tolerable salts thereof have valuable pharmacological and therapeutic properties, especially properties concerning the regulation of the metabolism of carbohydrates and lipids, enabling them to be used as medicaments especially in the treatment of metabolic illnesses, especially diabetes, obesity and their complications: dyslipaemiae, arterial hypertension, atheroma etc ..., and in the treatment of other neuroendocrinological disorders of any origin (dietetic, genetic, traumatic etc.).

The compounds I may also advantageously be prescribed together with other treatments used in the above-mentioned pathologies.

On chronic administration at doses of from 0.1 to 10 mg/kg from 1 to 3 times a day to obese rats having a glucose intolerance and a hyperinsulinaemia or a patent diabetes, the compounds correct the insulinaemia and the glucose tolerance in the glucose tolerance test via the intravenous route (according to V. CONARD, measure of the assimilation of glucose—theoretical bases and clinical applications—Edition Acta Medica Belgica—Brussels 1955).

The present invention also relates to pharmaceutical preparations containing as active ingredient a compound of the general formula I or a physiologically tolerable salt thereof, in admixture or association with an appropriate pharmaceutical excipient, such as, for example, distilled water, starch, talc, ethylcellulose or magnesium stearate.

The pharmaceutical preparations so obtained are generally in dosage form and may contain from 10 to 100 mg of active ingredient. They may take the form, for example, of tablets, dragees, gelatin-coated pills, suppositories, injectable or drinkable solutions and, depending on the cases concerned, may be administered orally, rectally or parenterally at a dose of from 10 to 100 mg from 1 to 3 times a day.

The following Examples illustrate the invention. The melting points are determined using a Kofler hot plate.

EXAMPLE 1

2-trifluoromethyl-6,7,8,9-tetrahydro-[5H]-benzocyclohepten-7-one

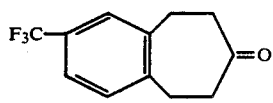

a) Preparation of 2-nitro-4-trifluoromethyliodobenzene:

A mixture of 87.6 ml of concentrated sulphuric acid and 46.8 ml of concentrated nitric acid (d=1.52) is prepared at 0° C. This mixture is added dropwise to 272 g of p-trifluoromethyliodobenzene maintained at 50° C., which takes about 1 hour, after which time the application of heat is ceased and stirring is continued for a further 30 minutes. The mixture is then hydrolysed by pouring onto 750 ml of water. The product is subsequently extracted three times with 600 ml of dichloromethane each time, and the organic phase is washed in succession with water and a 20% solution of sodium bicarbonate. The solvent is then evaporated and distillation yields 273 g of 2-nitro-4-trifluoromethyliodobenzene, b.p./8 mm=120°-125° C. (yield 86%).

b) Preparation of 2-amino-4-trifluoromethyliodobenzene:

A mixture of 225 ml of water, 166 g of iron and 10.03 g of ammonium chloride are heated to reflux. 317 g of 2-nitro-4-trifluoromethyliodobenzene are added thereto over a period of 2 hours, then refluxing is continued for 3 hours 30 minutes when the addition is complete. The whole is allowed to cool then the medium is extracted 4 times with 250 ml of benzene each time. The mixture is then filtered and subsequently decanted. The organic layer is dried and the solvent is evaporated. After distillation, 256 g of 2-amino-4-trifluoromethyliodobenzene are recovered, b.p.: 102° to 114° C., ind (25° C.): 1.556. (Yield: 89.5%).

c) 4-trifluoromethyl-1,2-diiodobenzene:

A mixture of 287 g of 2-amino-4-trifluoromethyliodobenzene and 417 ml of concentrated HCl are heated to 55° C. The mixture is cooled to a temperature maintained at from −10° to −15° C., and a solution of 38 g of sodium nitrite in 70 ml of water is added thereto while maintaining the temperature at from −10° to −15° C. 158 ml of concentrated HCl are then added followed by a further 38 g of sodium nitrite in 70 ml of water. The whole is then maintained at a temperature less than or equal to −10° C. for one hour while stirring. A solution of 250 g of potassium iodide in 400 ml of water is prepared; the solution is cooled to 0° C. and 54.3 ml of concentrated $H_2SO_4$ are added thereto while cooling. The diazo derivative solution obtained previously is added to this mixture while maintaining the temperature below 5° C. Once the addition is complete, the whole is maintained at room temperature for 15 minutes, then heated under reflux for half an hour and finally allowed to cool. The mixture is extracted 3 times with 1600 ml of ether each time, the extract is washed with a 12.5% solution of sodium bisulphite then with water, dried, and then the ether is distilled off. 377 g of 4-trifluoromethyl-1,2-diiodobenzene are obtained, m.p.: 62°-64° C. (Yield: 95%).

d) Preparation of 4-trifluoromethyl-1,2-di(β-methoxycarbonylvinyl)-benzene:

A mixture of 398 g of 4-trifluoromethyl-1,2-diiodobenzene, 224 ml of methyl acrylate, 24.3 g of tri-o-tolylphosphine, 4.5 g of palladium acetate, 342 ml of triethylamine and 1450 ml of anhydrous xylene is maintained at a temperature of approximately 80° C. for 36 hours while stirring. The heating is then ceased and the mixture is filtered. The residue is washed twice with 250 ml of xylene each time, then the xylene is distilled off in vacuo. The residue is washed with a mixture of cyclohexane and petroleum ether (25 ml/25 ml), and taken up in a minimum of diethyl ether. The ethereal phase is washed with water, decanted, dried and rendered colourless on animal black, and then the ether is distilled off. 236 g of 4-trifluoromethyl-1,2-di-(β-methoxycarbonylvinyl)-benzene are obtained. (Yield 75%).

e) Preparation of 4-trifluoromethyl-1,2-di-β-methoxycarbonylethyl)-benzene:

314 g of 4-trifluoromethyl-1,2-di-(β-methoxycarbonylvinyl)-benzene dissolved in 2200 ml of dimethylformamide and 1500 ml of methanol are hydrogenated under a pressure of 80-90 psi in the presence of approximately 300 ml of a suspension of Raney nickel. The mixture is then filtered, the solvent is distilled off and the practically pure crude oil collected is used as such. 305 g of 4-trifluoromethyl-1,2-di-(β-methoxycarbonyle-thyl)-benzene are obtained in this manner. (Yield≃96%).

f) Preparation of a mixture of 2-trifluoromethyl-6-methoxycarbonyl-6,7,8,9-tetrahydro-[5H]-benzocyclohepten-7-one and 2-trifluoromethyl-8-methoxycarbonyl-6,7,8,9-tetrayhydro[5H]-benzoocyclohepten-7-one:

44 g of sodium hydride suspension (60% in oil) are added to 1000 ml of xylene and the whole is heated to 90° C. A mixture of 318 g of 4-trifluoromethyl-1,2-di-(β-methoxycarbonylethyl)-benzene and 500 ml of xylene is added dropwise thereto while stirring. The whole is heated under reflux (once the evolution of gas has ceased) for approximately 4 hours. The temperature is brought to 20° C. 1000 ml of water is added to the mixture and the organic layer is extracted. The aqueous layer is washed three times with 500 ml of ether each time. The organic layers are combined and the solvents distilled off. The residual mixture is dried and used as such. 242 g of mixture are obtained (Yield≃85%).

g) Preparation of 2-trifluoromethyl-6,7,8,9-tetrahydro[5H]-benzocyclohepten-7-one:

285 g of the ketone ester mixture obtained above, 1000 ml of normal sodium hydroxide solution and 1000 ml of ethanol are refluxed for 15 minutes, after which the ethanol is removed by distillation under reduced pressure and the residual aqueous mixture is extracted 4 times with 1500 ml of diethyl ether each time. The organic layer is dried, taken up in a minimum of dichloromethane and purified by filtering over approximately 2000 g of silica or by recrystallisation from cyclohexane, to yield 168 g of 2-trifluoromethyl-6,7,8,9-tetrahydro-[5H]-benzocyclohepten-7-one, m.p.: 78° C. (Yield 74%).

EXAMPLE 2

2-trifluoromethyl-7-amino-6,7,8,9-tetrahydro-[5H]-benzocycloheptene

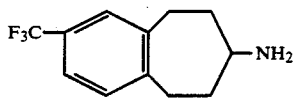

A mixture of 228 g of 2-trifluoromethyl-6,7,8,9-tetrahydro[5H]-benzocyclohepten-7-one, 69.5 g of hydroxylamine hydrochloride and 550 ml of pyridine are refluxed for 3 hours. The pyridine is distilled off under reduced pressure, and the residue is taken up in 2200 ml of water and extracted 4 times with 4000 ml of ether each time. The ethereal phases are dried, the ether is distilled off and the crude residue obtained (231 g), m.p. 117°-118° C., is used as such. (Yield≃95%). 243 g of the oxime obtained above are dissolved in a mixture of 1200 ml of ethanol and 5000 ml of ammoniacal ethanol, then hydrogenated under a pressure of 80-90 psi, first at room temperature then, after 1 hour 30 minutes, at 40° C. for a duration of 10 to 15 minutes. The reaction mixture is then filtered and the solvent is distilled off until a crude oily base is obtained. 222 g of 2-trifluoromethyl-7-amino-6,7,8,9-tetrahydro-[5H]-benzocycloheptene are obtained in this manner (yield≃97%). This base is purified in the form of a salt, especially in the form of a hydrochloride:

22.9 g of the base obtained above are dissolved in 200 ml of isopropanol. 25 ml of 4N hydrochloric acid-ether are added thereto while stirring. The precipitate formed is filtered and redissolved at elevated temperature in a minimum of the mixture CH$_2$Cl$_2$/CH$_3$OH (80/20). The mixture is progressively concentrated until precipitation occurs, the precipitate is filtered, washed with ether and dried to give an 80–85% yield of the hydrochloride of 2-trifluoromethyl-7-amino-6,7,8,9-tetrahydro-[5H]-benzocycloheptene, m.p. >260° C. with sublimation towards 300° C.

EXAMPLE 3

2-trifluoromethyl-7-(N-ethyl-N-formylamino)-6,7,8,9-tetrahydro-[5H]-benzocycloheptene

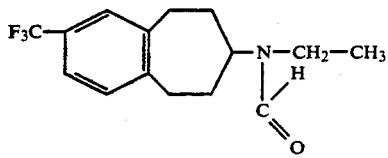

A mixture of 228.2 g of 2-trifluoromethyl-6,7,8,9-tetrahydro-[5H]-benzocyclohepten-7-one, 219 g of N-ethylformamide and 151 g of formic acid is heated under reflux for 14 hours. After concentration in vacuo, while heating on a bain-marie, the residue is taken up in 2300 ml of methylene chloride. After washing twice with 800 ml of water each time, the organic layer is dried over magnesium sulphate and, after filtration, the solvent is removed in vacuo. 283 g of 2-trifluoromethyl-7-(N-ethyl-N-formylamino)-6,7,8,9-tetrahydro-[5H]-benzocycloheptene are obtained in the form of an oil.

EXAMPLE 4

2-trifluoromethyl-7-N-ethylamino-6,7,8,9-tetrahydro-[5H]-benzocycloheptene

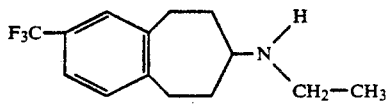

A mixture of 285.31 g of 2-trifluoromethyl-7-(N-ethyl-N-formylamino)-6,7,8,9-tetrahydro-[5H]-benzocycloheptene, 1150 ml of ethanol, 270 ml of concentrated hydrochloric acid (d: 1.19) and 215 ml of water are heated under reflux for 12 hours while stirring. The reaction mixture is then concentrated in vacuo while heating on a bain-marie. The residue is triturated with 2000 ml of anhydrous ether, and the precipitate is filtered and dried in air to yield 235 g of product melting at 190°–200° C. Recrystallisation from 400 ml of boiling isopropanol yields 150 g of 2-trifluoromethyl-7-N-ethylamino-6,7,8,9-tetrahydro-[5H]-benzocycloheptene, m.p.: 225° C.

EXAMPLE 5

2-trifluoromethyl-7-(N-ethyl-N-methylamino)-6,7,8,9-tetrahydro-[5H]-benzocycloheptene

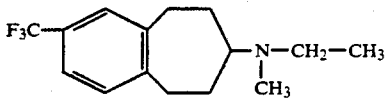

A solution of 285.3 g of 2-trifluoromethyl-7-(N-ethyl-N-formylamino)-6,7,8,9-tetrahydro-[5H]-benzocycloheptene in 3700 ml of anhydrous ether is introduced over a period of one hour into a suspension of 56 g of lithium aluminum hydride in 4700 ml of anydrous ether while stirring (a gentle reflux is observed). The whole is then heated at the boil for 5 hours. After cooling, the reaction mixture is hydrolysed in succession with 56 ml of water, 56 ml of a solution of 4N sodium hydroxide and 170 ml of water. After filtration and washing with ether, the organic layer is concentrated in vacuo and the residue is distilled off. 150 g of 2-trifluoromethyl-7-(N-ethyl-N-methylamino)-6,7,8,9-tetrahydro-[5H]-benzocycloheptene are obtained, b.p./$_{10\ mm}$=135°–140° C.

EXAMPLE 6

2-trifluoromethyl-7-(N-ethoxycarbonylmethylamino)-6,7,8,9-tetrahydro-[5H]-benzocycloheptene

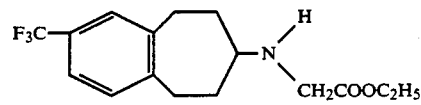

458.5 g (2 mols) of 2-trifluoromethyl-7-amino-6,7,8,9-tetrahydro-[5H]-benzocycloheptene are dissolved in 2000 ml of anhydrous benzene. One mol of ethyl bromoacetate is added thereto and the whole is heated under reflux. A precipitate forms. The refluxing is maintained for 4 hours, then the mixture is allowed to return to room temperature. The hydrobromide precipitate of the starting amine is filtered off and washed in benzene then ether. The solvent is distilled off from the filtrate. The oil obtained is used as such for the subsequent hydrolysis. Ultimately 271 g of 2-trifluoromethyl-7-(N-ethoxycarbonylmethylamino)-6,7,8,9-tetrahydro-[5H]-benzocycloheptene are obtained. (Yield 86%), a sample of which is purified in the form of the hydrochloride, which sublimes towards 270°–280° C.

EXAMPLE 7

2-trifluoromethyl-7-(N-carboxymethylamino)-6,7,8,9-tetrahydro-[5H]-benzocycloheptene

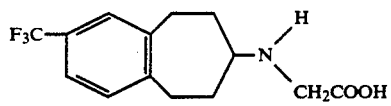

315.34 g (1 mol) of 2-trifluoromethyl-7-(N-ethoxycarbonylmethylamino)-6,7,8,9-tetrahydro-[5H]-benzocycloheptene are heated at reflux for approximately 25 minutes in a mixture of 1000 ml of normal sodium hydroxide and 2200 ml of ethanol. The ethanol is then distilled off terminating under reduced pressure, and the aqueous phase is washed twice with 4000 ml of diethyl ether each time. The ethereal phases are washed with water again. 1000 ml of a normal hydrochloric acid solution are added to the combined aqueous phases. The precipitate obtained is collected and washed. 250 g of 2-trifluoromethyl-7-(N-carboxymethylamino)-6,7,8,9-tetrahydro-[5H]-benzocycloheptene are obtained, which sublimes above 260° C. (Yield 87%). By adding a stoichiometric amount of hydrochloric acid and recrystallising from water, the hydrochloride of this amino acid, which sublimes towards 220°–222° C., is obtained.

EXAMPLE 8

2-trifluoromethyl-7-(N-acetylamino)-6,7,8,9-tetrahydro-[5H]-benzocycloheptene

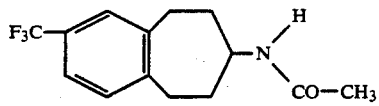

1 mol of 2-trifluoromethyl-7-amino-6,7,8,9-tetrahydro-[5H]-benzocycloheptene and 1 mol of triethylamine are introduced into 10000 ml of diethyl ether. 1 mol of $CH_3COCl$ is slowly added to this mixture, then the whole is heated under reflux for 30 minutes while stirring. The whole is allowed to cool, the ether is distilled off under reduced pressure, and the residue obtained is taken up in water and filtered. Recrystallisation from ethyl acetate yields 250 g of 2-trifluoromethyl-7-N-acetylamino-6,7,8,9-tetrahydro-[5H]-benzocycloheptene, melting at 216°–217° C. with slight sublimation. (Yield 92%).

EXAMPLE 9

2-trifluoromethyl-7-(β-aminoethyl-6,7,8,9 tetrahydro-[5H]-benzocycloheptene

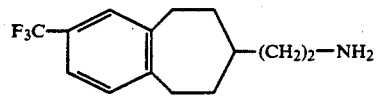

8.85 g of ethylcyanomethylenephosphate are added to a suspension of sodium hydride (0.05 mol) (washed with petroleum ether) in 75 ml of anhydrous dimethylformamide, while stirring, for 30 minutes.

The temperature is raised to 50° C. until the evolution of gas ceases. The temperature is allowed to return to room temperature, then 11.4 g of 2-trifluoromethyl benzocyclohepten-7-one in solution in 25 ml of dimethylformamide, are added, for 10 minutes. The temperature raised to 43° C.

The recation mixture is then maintained at 80° C. for one hour and a half. After cooling, the mixture is taken off by 50 ml of water and 150 ml of ether. After stirring, decantation and drying of the organic layer on MgSO4, the solvent is evaporated. 12.5 g of 2-trifluoromethyl-7-chloromethylene-benzocycloheptene, melting at 70° C., are obtained 6 g of the so-obtained product are hydrogenated, in solution in 150 ml of anhydrous dimethylformamide, in the presence of 2.5 g of palladium carbon black at 5%, under 60 lb/s.inch.

After the completion of the absorption,. the catalyst is suctioned off and the filtrate concentrated in vacuo. 6 g of 2-trifluoromethyl-7-cyanomethyl benzocycloheptene are obtained.

The so-obtained product, in solution in 20 ml of anhydrous ether, is poured, while stirring, onto a suspension of 1 g of lithium-aliminum hydride in 100 ml of anhydrous ether for 30 minutes. at a temperature within the range of from-10° to 15° C. The stirring is maintained for one hour, at room temperature then the reaction mixture is hydrolyzed with aqueous sodium hydroxyde, suctioned off and the filtrate is dried on MgSO4.

The solvent is evaporated and the remaining oil (5.2 g) is dissolved in 25 ml of anhydrous ether. 7 ml of a 3N solution of hydrochloric acid in ether are added.

The so-formed precipitate is suctioned off and dried in vacuo to yield 2.8 g of 2-trifluoromethyl-7-(β-aminoethyl)-6,7,8,9-tetrahydro-[5H]-benzocycloheptene hydrochloride, M.P.: 180°–181° C.

EXAMPLE 10

2-trifluoromethyl-7-n.butylamino-6,7,8,9-tetrahydro-[5H]-benzocycloheptene 1.95 g of potassium cyanide in solution in 7.5 ml of water, are added, for 5 minutes, to a suspension of 6.8 g of 2-trifluoromethylbenzocyclohepten-7-one and 3.25 g of n.butylamine hydrochloride in 6 ml of methanol. The suspension becames fluid and the temperature reaches 29° C.

The reaction mixture is stirred for 24 hours at room temperature then heated to reflux for 3 hours.

After cooling the mixture is taken off by 50 ml of methylene chloride, decanted off, washed twice with 25 ml of water each time, dried on MgSO4 and concentrated in vacuo. 9.5 g of 2-trifluoromethyl-7-n.butylamino-7-cyano-benzocycloheptene are obtained.

The so obtained product is dissolved in 200 ml of anhydrous benzene. 6.7 g of potassium tertiobutylate are added and the whole is heated to reflux while stirring for 3 hours. After cooling, the suspension is filtred and the filtrate is concentrated in vacuo. 6.5 g of 2-trifluoromethyl-7-n.butylimino-7 benzocycloheptene are obtained.

The so-obtained product is dissolved in 150 ml of methanol and hydrogenated, in the presence of 0.7 g de platine oxyde in a PARR flask under a pressure of 60 lb/s.inch.

After stirring for one hour, the absorption being finished, the catalyst is suctioned off, and the filtrate is concentrated in vacuo.

The residual oil (6 g) is taken off with 50 ml of anhydrous isopropanol; 4.3 ml of a 3N solution of Hcl in ether are added and the solution is allowed at rest.

After 24 hours at room temperature, the so-formed precipitate is suctioned off and dried. 3.8 g of 2-trifluoromethyl-7-n.butylamino-6,7,8,9-tetrahydro-[5H]-benzocycloheptene hydrochloride, M.P.: 234° C., are obtained.

EXAMPLE 11

2-trifluoromethyl-7-hydroxy-7-aminomethyl-6,7,8,9-tetrahydro-[5H]-benzocycloheptene

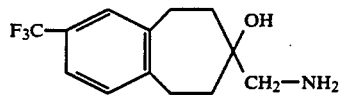

A solution of 3.9 g of potassium cyanide in 8 ml of water is added, at 10° C., for 30 minutes, to a stirred suspension of 2-trifluoromethylbenzocyclohepten-7-one in 5.6 ml of acetic anhydrid.

The temperature rises up to 25° C. After stirring at toom temperature for 4 hours, the reaction mixture is poured on 50 ml of a 10% aqueous solution of sodium bicarbonate.

The whole is extracted with ether, washed with water, dried and concentrated. 7.5 g of a solid product, melting at 110°–113° C., are obtained. This solid product is taken off with 16 ml of acetic anhydrid and 0.8 ml of acetyl chloride.

The mixture is stirred and allowed at rest for 24 hours, then neutralised with 250 ml of a 10% solution of sodium bicarbonate, extracted with ether, washed with water, dried and the solvent is evaporated off. 8.8 g of 2-trifluoromethyl-7-acetoxy-7-cyanobenzocycloheptene (oil) are obtained. The so obtained product, in solution in 30 ml of anhydrous ether is poured, while stirring, in a suspension of 2.5 g of lithium aluminum hydride. The reaction mixture is refluxed for 4 hours then hydrolysed. 7.2 g of an oil is obtained.

This oil is taken off with 50 ml of anhydrous ethyl acetate and treated with 10 ml of a 3N solution of HCl in ether, to yield, after suction and drying of the precipitate, 6.7 g of 2-trifluoromethyl-7-hydroxy-7-aminomethyl-6,7,8,9-tetrahydro-[5H]-benzocycloheptene hydrochloride, M.P.: 217° C.

EXAMPLE 12

2-trifluoromethyl-7-methyl-7-ethylamino-6,7,8,9-tetrahydro-[5H]-benzocycloheptene

11.4 g of 2-trifluoromethyl benzocyclohepten-7-one in solution in 90 ml of anhydrous tetrahydrofuran are added, for 30 minutes while stirring, to a magnesium methyl iodide solution prepared starting from 9.2 g of methyl iodide and 1.6 g of magnesium in turnings in 90 ml of anhydrous ether.

The mixture is refluxed for 3 hours, then hydrolysed with 25 ml of water; the aqueous layer is decanted off, the organic layer is dried on MgSO4 and the solvent is evaporated in vacuo. 13 g of 2-trifluoromethyl-7-hydroxy-7-methyl benzocycloheptene are obtained.

40 ml of pure acetic acid are added to 10 g of concentrated sulfuric acid, at a temperature lower than 15° C.; then 13 g of the previously obtained product in solution in 10 ml of acetic acid are added for 10 minutes at a temperature lower than 15° C.

The reaction mixture is allowed to reach room temperature then heated to 50°-55° C. for 2 hours. After cooling, it is treated with 200 g of a water-ice mixture and extracted with ether.

After drying and evaporation of the solvent in vacuo, 8.7 g of 2-trifluoromethyl-7-methyl-7-acetylamino benzocycloheptene are obtained. This product, dissolved in 85 ml of anhydrous tetrahydrofuran is poured in a stirred suspension of 1.5 g of lithium aluminum hydride in 120 ml of anhydrous ether. The reaction mixture is refluxed for 7 hours, hydrolysed, and suctioned off. The filtrate is dried on MgSO4 and concentrated in vacuo. 4.8 g of an oil are obtained.

This oil is taken up with 50 ml of isopropanol then treated with 6 ml of a 4.3N solution of Hcl in ether, to yield a precipitate which is suctioned off, washed and dired in vacuo to yield 4.8 g of 2-trifluoromethyl-7-methyl-7-ethylamino-6,7,8,9-tetrahydro-[5H]-benzocycloheptene hydrochloride, M.P.>260° C.

EXAMPLES 13 to 33

The following derivatives are prepared in accordance with the methods described above:

13) 2-trifluoromethyl-7-methylamino-6,7,8,9-tetrahydro-[5H]-benzocycloheptene.

14) 2-trifluoromethyl-7-N-propylamino-6,7,8,9-tetrahydro-[5H]-benzocycloheptene, M.P. of the corresponding hycrochloride: 231° C.

15) 2-trifluoromethyl-7-N-propionylamino-6,7,8,9-tetrahydro-[5H]-benzo-cycloheptene.

16) 2-trifluoromethyl-7-N-butyrylamino-6,7,8,9-tetrahydro-[5H]-benzocycloheptene 17) 2-trifluoromethyl-7-N-hydroxyethylamino-6,7,8,9-tetra-hydro-[5H]-benzo-cycloheptene, M.P. of the corresponding hydrochloride: 175° C.

18) 2-trifluoromethyl-7-N-diethylamino-6,7,8,9-tetrahydro-[5H]-benzocycloheptene.

19) 2-trifluoromethyl-7-N-dipropylamino-6,7,8,9-tetrahydro-[5H]-benzocycloheptene (oil).

20) 2-trifluoromethyl-7-N-dimethylamino-6,7,8,9-tetrahydro-[5H]-benzocycloheptene.

21) 2-trifluoromethyl-7-(N-methyl-N-propylamino)-6,7,8,9-tetrahydro-[5H]-benzocycloheptene, M.P. of the corresponding hydrochloride: 185° C.

22) 2-trifluoromethyl-7-piperidino-6,7,8,9-tetrahydro-[5H]-benzocycloheptene.

23) 2-trifluoromethyl-7-morpholino-6,7,8,9-tetrahydro-[5H]-benzocycloheptene.

24) 2-trifluoromethyl-7-N-piperazinyl-6,7,8,9-tetrahydro-[5H]-benzocycloheptene.

25) 2-trifluormethyl-7-7N-imidazolidinyl-6,7,8,9-tetrahydro-[5H]-benzocycloheptene.

26) 2-trifluormethyl-7-N-propylidene-amino-6,7,8,9-tetrahydro-[5H]-benzocycloheptene.

27) 2-trifluoromethyl-7-N-benzoyloxyethylamino-6,7,8,9-tetrahydro-[5H]-benzocycloheptene, M.P. of the corresponding hydrochloride: 229°-230° C., with sublimation.

28) 2-trifluoromethyl-7-hydroxy-6,7,8,9-tetrahydro-[5H]-benzocycloheptene, M.P.: 80°-85° C.

29) 2-trifluoromethyl-7-[N-ethyl-N-($\beta$-aminoethyl)amino]-6,7,8,9-tetrahydro-[5H]-benzocycloheptene, M.P. of the corresponding hydrochloride >260° C.

30) 2-trifluoromethyl-7-[N-ethyl-N-($\beta$-acetylaminoethyl) amino]-6,7,8,9-tetra-hydro-[5H]-benzocycloheptene M.P. of the corresponding hydrochloride: 167°-168° C.

31) 2-trifluoromethyl-7-aminomethyl-6,7,8,9-tetrahydro-[5H]-benzocycloheptene, M.P. of the corresponding hydrochloride: 198°-199° C.

32) d.2-trifluoromethyl-7-amino-6,7,8,9-tetrahydro-[5H]-benzocycloheptene, the physical constants of the corresponding hydro-chloride are: M.P.>260° C. (isopropanol) [$\alpha$] (C=1%, CH3OH): 546:+4.9; 436:+6.3; 365:+5.7.

33) 1.2-trifluoromethyl-7-amino-6,7,8,9-tetrahydro-[5H]-benzocycloheptene, the physical constants of the corresponding hydrochloride are: M.P. >260° C. (isopropanol) [$\alpha$] (C=1%, CH3OH): 546:−4.9; 436:−6.3; 365:−5.7.

We claim:

1. A compound selected from the group consisting of: benzocycloheptenes of the formula I

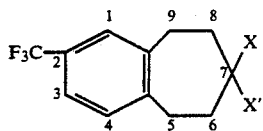 (I)

in which

1) X represents hydrogen, straight chain or branched alkyl having 1 to 5 carbon atoms, cyano, or hydroxy:
2) X' represents:
   a) hydroxy,
   b) OR in which R represents:
   α) COR' in which R' represents
      straight chain or branched alkyl having 1 to 5 carbon atoms unsubstituted or substituted by phenyl, or
      phenyl unsubstituted or substituted by one or more halogen atoms, or by alkyl or alkoxy having 1 to 5 carbon atoms; or
   β) straight chain or branched alkyl having 1 to 5 carbon atoms unsubstituted or substituted by carboxy or phenyl;
   c) a radical of the formula:

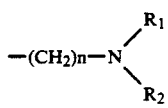

in which:
   n represents 0, 1, or 2 and
   $R_1$ and $R_2$, which may be the same or different, each represents:
   hydrogen;
   straight-chain or branched alkyl having 1 to 5 carbon atoms, unsubstituted or substituted by hydroxy, amino, carboxy, alkoxycarbonyl having 1 to 6 carbon atoms or acyloxy of the formula R'—COO— in which R' has the meaning above defined;
   alkenyl having 2 to 5 carbon atoms;
   alkynyl having 2 to 5 carbon atoms;
   acyl of the formula R"—CO— in which R" represents straight chain or branched alkyl having 1 to 5 carbon atoms, phenyl, or phenylsulfonylamino, the phenyl moiety of which is unsubstituted or substituted by one or more halogen atoms, trifluoromethyl, alkyl or alkoxy having 1 to 5 carbon atoms; or
   $R_1$ and $R_2$ together with the nitrogen atom to which they are bonded represent

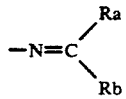

in which:
   Ra represents hydrogen or straight chain or branched alkyl having 1 to 5 carbon atoms, and Rb represents hydrogen, straight chain or branched alkyl having 1 to 5 carbon atoms, phenyl, or phenylalkyl;
   or $R_1$ and $R_2$ together represent the remainder of a five- or six-membered heterocyclic ring which may contain an additional hetero atom selected from oxygen and nitrogen; or
3) X and X' together represent:

in which:
   $R_3$ represents straight chain or branched alkyl having 1 to 5 carbon atoms, unsubstituted or substituted by:
   cyano,
   —COOR''' in which R''' represents hydrogen or alkyl having 1 to 5 carbon atoms, or
   phenyl, unsubstituted or substituted by one or more halogen atoms, or by alkyl or alkoxy having 1 to 5 carbon atoms;
   an enantiomer thereof, and
   a pharmaceutically-acceptable acid addition salt thereof.

2. A compound of claim 1, having the formula I':

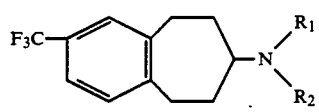 (I')

in which $R_1$ and $R_2$ have the meanings defined in claim 1.

3. A compound of claim 1 which is: 2-trifluoromethyl-7-amino-6,7,8,9-tetrahydro-[5H]-benzocycloheptene.

4. A compound of claim 1 which is: 2-trifluoromethyl-7-(N-ethyl-N-formylamino)-6,7,8,9-tetrahydro-[5H]-benzocycloheptene.

5. A compound of claim 1 which is: 2-trifluoromethyl-7-N-ethylamino-6,7,8,9-tetrahydro-[5H]-benzocycloheptene.

6. A compound of claim 1 which is: 2-trifluoromethyl-7-(N-ethyl-N-methylamino)-6,7,8,9-tetrahydro-[5H]-benzocycloheptene.

7. A compound of claim 1 which is: 2-trifluoromethyl-7-(N-ethoxycarbonylmethylamino)-6,7,8,9-tetrahydro-[5H]-benzocycloheptene.

8. A compound of claim 1 which is: 2-trifluoromethyl-7-(N-carboxymethylamino)-6,7,8,9-tetrahydro-[5H]-benzocycloheptene.

9. A compound of claim 1 which is selected from the group consisting of d.2-trifluoromethyl-7-amino-6,7,8,9-tetrahydro-[5H]-benzocycloheptene and a pharmaceutically-acceptable acid addition salt thereof.

10. A compound of claim 1 which is d.2-trifluoromethyl-7-amino-6,7,8,9-tetrahydro-[5H]-benzocycloheptene hydrochloride.

11. A pharmaceutical composition suitable for treating a metabolic illness containing as active ingredient a compound according to claim 1, together with a pharmaceutically-acceptable carrier or diluent.

12. A method for treating a living animal afflicted with a metabolic illness, comprising the step of administering to the said living animal an amount of a compound of claim 1 which is effective for alleviation of the said condition.

* * * * *

UNITED STATES PATENT AND TRADEMARK OFFICE
CERTIFICATE OF CORRECTION

PATENT NO. : 5,079,245

DATED : Jan. 7, 1992

INVENTOR(S) : Michel Wierzbicki, Pierre Hugon, Jacques Duhault, Francoise Lacour It is certified that error appears in the above-identified patent and that said Letters Patent is hereby corrected as shown below:

```
Title Page, [54], line 1; "-SUBSTITUTE-" should read
  -- SUBSTITUTED- --.
Title Page [57] ABSTRACT, last line; "benzocycloheptane."
  should read -- benzocycloheptene. --.
Column 1, line 1; (disregard marginal numbering) "-SUBSTITUTE-"
  should read -- -SUBSTITUTED- --
Column 1, line 31; "atraight" should read -- straight --.
Column 1, line 54; "whicch" should read -- which --.
Column 3, line 43; "atoms;" should read -- atom; --.
Column 9, line 59; "di-β-" should read -- di-(β - --.
Column 13, line 44; "recation" should read -- reaction --.
Column 13, line 61; delete the period after "minutes".
Column 13, line 64; "hydroxyde," should read -- hydroxide, --.
Column 14, line 14; "becames" should read -- becomes --.
Column 14, line 39; "at rest." should read -- to rest. --
Column 14, line 61; "toom" should read -- room --.
Column 15, line 1; "at" should read -- to --.
Column 15, approximately line 61; "dired" should read -- dried --.
```

Signed and Sealed this

Thirty-first Day of August, 1993

*Attest:*

BRUCE LEHMAN

*Attesting Officer*     *Commissioner of Patents and Trademarks*